United States Patent [19]

Mortensen et al.

[11] Patent Number: 5,541,069
[45] Date of Patent: Jul. 30, 1996

[54] ASSAY HAVING IMPROVED DOSE RESPONSE CURVE

[75] Inventors: Richard B. Mortensen, Menlo Park; Henry K. Tom, La Honda, both of Calif.

[73] Assignee: Quidel Corporation, San Diego, Calif.

[21] Appl. No.: 843,681

[22] Filed: Feb. 28, 1992

[51] Int. Cl.⁶ .................... G01N 33/535; G01N 33/536; G01N 33/538; G01N 33/74

[52] U.S. Cl. .................... 435/7.9; 435/188; 435/962; 436/518; 436/63; 436/5.37; 436/540; 422/57; 422/58; 422/100; 422/101

[58] Field of Search .................... 435/7.9, 188, 962; 436/518, 63, 537, 540, 807, 825; 422/57, 58, 100, 101

[56] References Cited

U.S. PATENT DOCUMENTS

| | | | |
|---|---|---|---|
| 4,818,677 | 4/1989 | Hay-Kaufman et al. | 435/4 |
| 4,920,046 | 4/1990 | McFarland et al. | 435/7.31 |
| 4,943,522 | 7/1990 | Eisinger et al. | 435/7.25 |
| 4,952,517 | 8/1990 | Bahar | 436/518 |
| 5,028,535 | 7/1991 | Buechler et al. | 435/7.1 |
| 5,079,170 | 1/1992 | Rosman et al. | 436/178 |

FOREIGN PATENT DOCUMENTS

| | | |
|---|---|---|
| 0327843 | 8/1989 | European Pat. Off. . |
| WO90/08319 | 7/1990 | WIPO . |

OTHER PUBLICATIONS

D. Catty et al "ELISA and Related Enzyme Immunoassays" in *Antibodies vol. II a Practical Approach* Ed. D. Catty 1989 IRL Press pp. 97–154.

*Primary Examiner*—James C. Housel
*Assistant Examiner*—Nancy Parsons
*Attorney, Agent, or Firm*—Townsend and Townsend and Crew LLP

[57] ABSTRACT

An assay for determining the presence of a threshold concentration of an analyte in a sample comprises first reacting the sample with an amount of anti-analyte selected to reduce the free analyte to a marginally detectable concentration. The sample is then contacted with anti-analyte immobilized on a test region or indicator zone on a solid phase, whereby the residual free analyte may be bound. The binding of free analyte to immobilized anti-analyte is detected by a variety of techniques to indicate the presence of the threshold concentration. By employing limited amounts of anti-analyte on the solid phase, the change between maximum binding of label and no binding of label will be responsive to very small changes in the analyte concentration originally present in the sample.

28 Claims, 1 Drawing Sheet

ASSAY HAVING IMPROVED DOSE RESPONSE CURVE

BACKGROUND OF THE INVENTION

The present invention relates generally to immunoassays for analyte detection and more particularly to immunoassays which rely on a change in a signal to detect analyte concentrations which exceed a preselected threshold value.

Immunoassays which produce a visual signal, such as color change, fluorescence, luminescence, or the like, are particularly useful for the detection of threshold concentrations of an analyte. Desirably, such immunoassay systems will provide an extreme signal condition when the concentration of analyte in a sample is below the preselected concentration value and will provide the opposite extreme signal condition when the analyte concentration exceeds the concentration value even by a small amount.

Of particular interest to the present invention are membrane assays of the type described in U.S. Pat. No. 4,818,677, and lateral flow assays of the type described in U.S. Pat. No. 4,943,522, the disclosures of which are incorporated herein by reference. Certain membrane assays utilize a reaction cell having a microporous membrane placed over an absorbant capable of drawing a liquid sample perpendiculary through the membrane. A capture reagent, typically an antibody, specific for the analyte is immobilized on the membrane. Sample which is applied to the membrane is drawn therethrough by the absorbant, with any analyte present being captured by the reagent. Signal can be produced by further applying labelled antibodies or other reagents which specifically recognize the analyte and mediate the production of a signal, such as color, fluorescence, or luminescence.

Lateral flow assays also utilize a porous membrane for performing a detection reaction. Instead of drawing the sample through the membrane perpendicularly, however, the sample is permitted to flow laterally from an application zone to a reaction zone on the membrane surface. The capture reagent is present in the reaction zone, and the captured analyte can be detected by a variety of protocols, including direct visualization of visible moieties associated with the captured analyte (as described in copending application Ser. No. 07/639,967, the disclosure of which is incorporated herein by reference).

By employing antibodies having a high affinity for the analyte as the capture reagent, a steep or rapid change in the visual signal can be achieved. That is, the signal will change over a very narrow concentration band. While such a rapid or sharp change is desirable, it is also necessary that the change occur at the concentration value of interest. If the signal change occurs above or below the concentration value of interest, the information provided by the assay will be of reduced value.

One approach for altering the detected concentration value is described in U.S. Pat. No. 4,952,517, and European Patent Appln. No. 327 843. A sample having an unknown amount of analyte is combined with a preselected threshold amount of free anti-analyte. The anti-analyte binds the analyte, with unbound anti-analyte remaining only if the original analyte concentration in the sample was below the threshold value (determined by the preselected amount of free anti-analyte). The sample is then contacted with a limited amount of immobilized analyte which will bind to free anti-analyte remaining in the sample. By then exposing the immobilized analyte to labelled anti-analyte, label will bind only if the analyte concentration in the sample was below the threshold concentration. The bound label can then be detected by a variety of conventional techniques to produce a visual signal. Thus, by properly selecting the concentration of free anti-analyte added to the sample and the amount of immobilized analyte, both the concentration detected and the range over which the signal changes from minimum to maximum can be controlled.

While generally workable, the sensitivity of this method is generally limited by the amount of immobilized analyte reacted with the sample (i.e., the method is not suitable for detecting threshold amounts lower than the amount of immobilized analyte). Moreover, high analyte concentrations in the sample can interfere with the results of the assay. That is, excessive amounts of free analyte could be carried over and bind the labelled anti-analyte, affecting the result. Additionally, the concentration range of analyte is limited by the amount of immobilized analyte.

A second approach for performing visual signal immunoassays for detecting preselected concentration values is described in U.S. Pat. No. 5,028,535, and corresponding PCT application WO 90/08319. A sample containing an unknown amount of native analyte is contacted with known amounts of labelled analyte and analyte receptor, usually anti-analyte antibody, to form a reaction mixture. Competition between the labelled analyte and the unknown (unlabelled) analyte for binding to the analyte receptor occurs, with the amount of labelled analyte remaining unbound being directly proportional to the amount of unknown analyte originally present in the sample. After separation, the amount of unbound labelled analyte can be detected by conventional visual detection systems and related directly to the amount of analyte initially present in the sample.

While generally workable, these detection systems rely on competition between native analyte and labelled analyte, requiring time to reach equilibrium. Moreover, the sensitivity of the assay may be limited by the amount of analyte receptor and the time delay in reaching equilibrium. Additionally, the assay system may be influenced by interfering substances which disrupt the binding between the analyte receptor and the analyte/labelled analyte. Also, the labelled analyte frequently will bind more strongly to the analyte receptor than the native analyte, adversely affecting the assay results.

Thus, it would be desirable to provide improved immunoassay formats which provide a visual signal which is related to a preselected concentration value of an analyte of interest. The visual signal should define a sharp end point, that is, should change from a minimum or zero value signal to a distinctly different signal over a very narrow concentration range centered at the preselected concentration value. The concentration value at which the visual signal changes should be independently selectable so that it can be correlated with a measurement value of interest. It would be further desirable if the selected concentration value could be programmed into the assay without the need to perform an additional step. Additionally, the assay of the present invention should overcome the disadvantages described above in connection with previous immunoassay systems.

SUMMARY OF THE INVENTION

The present invention comprises improved assay methods and kits for detecting threshold concentrations of an analyte in a sample. The assay method comprises reacting the sample with a predetermined first amount of an anti-analyte, usually an antibody specific for the analyte, selected to reduce the quantity of free analyte available in the reacted sample to a preselected level. In particular, the first amount of free antibody reacted with the sample is selected so that native analyte concentrations which are slightly below the threshold concentration will result in reacted samples having substantially no residual free analyte available for detection. Conversely, samples containing native analyte at a concentration even slightly above the threshold concentration will result in residual free analyte concentrations which are significantly above the marginally detectable level. Thus, the presence of native analyte in the sample at the threshold concentration can be detected with great sensitivity and accuracy. Moreover, the threshold concentration detected can be adjusted by changing the amount of free anti-analyte reacted with the sample without other significant modifications to the assay system.

The first amount of anti-analyte can be reacted with the sample by combining the sample and the anti-analyte in a separate reaction mixture, typically requiring an additional assay step. A quantity of the reacted sample can then be used in the remaining assay steps. Preferably, however, the sample will be reacted with the anti-analyte as part of another assay step, such as sample transfer (e.g., where the first amount anti-analyte is immobilized on or in a transfer pipette or filter); sample application (e.g., where the first amount of anti-analyte is immobilized in an application zone of a lateral flow assay device), or any other assay step which occurs prior to sample capture. In this way, the number of assay steps can be reduced and assay reliability increased.

After reacting the sample with the anti-analyte, the reacted sample is contacted with additional anti-analyte immobilized on a solid phase. The solid phase is thus able to bind the remaining free analyte which can then be separated by removing the solid phase from the sample. The amount of analyte bound to the solid phase can then be detected by conventional techniques and related to the presence of the threshold concentration of analyte originally present in the sample.

The detection will usually be based on the production of a visible signal, where an extreme signal condition is produced when there is no residual analyte remaining in the reacted sample and an opposite extreme signal condition is produced when the residual analyte exceeds a marginally detectable level. Exemplary extreme signal conditions include color:no color; light:no light; fluorescence:no fluorescence, and the like.

In a first exemplary embodiment of the present invention, the reacted sample is passed perpendicularly through a porous test membrane. Binding of residual analyte occurs at the site where the reacted sample is applied and the presence of bound analyte is detected by contacting the membrane with an analyte-labeled conjugate, typically enzyme-labelled analyte. The amount of immobilized anti-analyte on the membrane is limited so that excess residual free analyte in the reacted sample will block substantially all available sites for binding the analyte-label conjugate, resulting in no label binding to the solid phase. Conversely, with native analyte concentrations which fall appreciably below the threshold concentration, there will remain little or no available free analyte after reaction with the free antibody. Thus, substantially all binding sites on the solid phase will be able to bind to analyte-label conjugate, resulting in a maximum signal on the solid phase.

In this first embodiment, the sample may be reacted with the first amount of anti-analyte in a separate reaction mixture, where all or a portion of the liquid reaction mixture may be applied to the membrane. Alternatively, the applicator used to transfer sample to the membrane may contain immobilized anti-analyte which can bind and sequester the analyte as part of the sample transfer step. It would also be possible to incorporate immobilized anti-analyte in a matrix which is used to filter the sample being applied to the membrane. Other approaches will also be available.

In a second exemplary embodiment, the reacted sample is caused to flow laterally from an application zone to a reaction zone within a porous test membrane. Binding of residual analyte (and optionally signal producing components) occurs as the reacted sample flows through the reaction zone which contains an appropriate amount of anti-analyte. Binding between the residual analyte and the anti-analyte can be detected by a variety of protocols, with single-step protocols being preferred.

In a specific aspect of the second exemplary embodiment, the first amount of anti-analyte can be immobilized within the application zone and/or the membrane region. In this way, the desired amount of free analyte can be bound as part of the sample application step, without the need to perform a separate step. Of course, any of the other free analyte sequestering techniques described in connection with the first exemplary embodiment of the present invention could also be employed.

In another specific aspect of the present invention (applicable to both of the first and second exemplary embodiments), semi-quantitative results can be obtained by employing different amounts of "first" anti-analyte with respect to different regions of a test region or membrane. Thus, each region of the test membrane will correspond to a different threshold concentration of analyte, permitting detection of concentration ranges. Such semi-quantitative assays may be conveniently performed using the lateral flow test membranes, where a plurality of lanes are performed with each lane having a different amount of anti-analyte immobilized within the application zone.

The assay kit of the present invention will include containers for holding the necessary reagent(s) test membrane(s) sample applicator(s) filter(s), and the like, as well as instructions which set forth a protocol for practicing the method as just described. Typically, the components of the kit will be present in a suitable package containing sufficient components for performing one or more assays.

The assay and kits of the present invention are particularly well suited for detecting threshold concentrations of small molecules in biological samples, such as hormones, hormone metabolites, and drugs present in urine, saliva, and blood samples. The assays provide for highly sensitive detection of such threshold concentrations, particularly when high affinity anti-analytes are employed. The assay protocol allows for a substantially arbitrary selection of the threshold concentration to be detected by employing varying amounts of the first anti-analyte to block or sequester desired amounts of the native analyte in the sample.

DESCRIPTION OF THE SPECIFIC EMBODIMENTS

Figure 1:
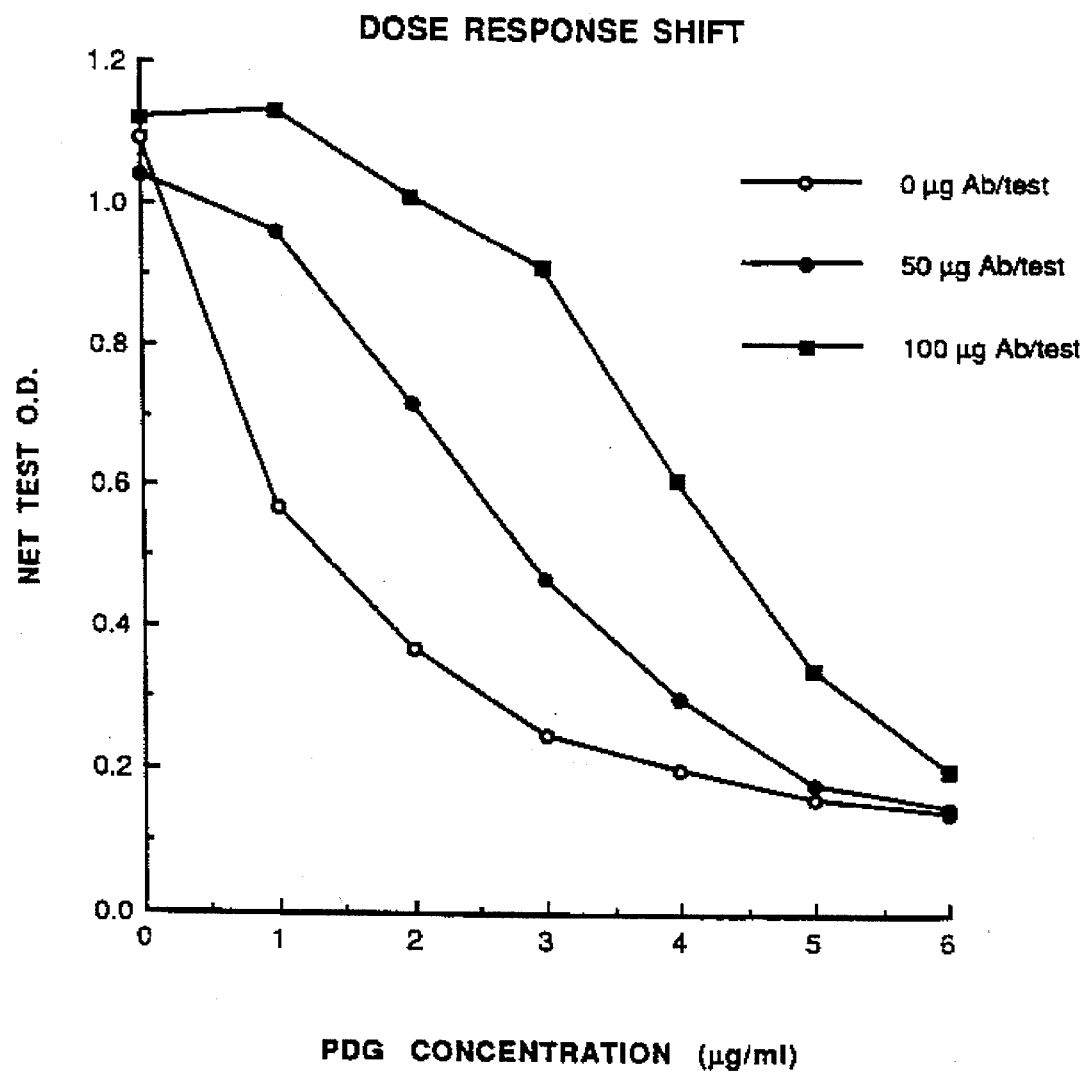
FIG. 1 illustrates the results of a comparative example in the Experimental section, with dose response curves for assays run with and without addition of anti-analyte (free antibody) addition, showing the shift in the dose response curve which results from such anti-analyte addition.

A method and kit are provided for detecting the presence of a threshold concentration of an analyte in a sample. The actual concentration of native analyte in the sample may vary widely, and the present invention provides a detectable change in a signal, usually a visual signal, when the threshold concentration is present or exceeded. The value of the threshold concentration can be selected within fairly wide limits by properly selecting the amounts and concentrations of reagents used in the assay, as will be described in greater detail hereinafter. Optionally semi-quantitative concentration determinations can be made by simultaneously measuring a plurality of threshold concentrations in the same sample.

The present invention relies on blocking or sequestering a predetermined amount of native analyte present in the sample by initially reacting the sample with a first predetermined amount of an anti-analyte, usually a free or immobilized antibody with a high binding affinity for the analyte. The amount of anti-analyte will be sufficient to reduce the native analyte in the combined sample by a preselected differential amount to leave a variable residual amount, where the variable residual amount is readily detectable in the subsequent detection phase of the assay. Usually, the differential amount will be selected to leave little or no residual analyte when the actual amount of analyte present in the sample is below the threshold amount, i.e., the differential amount will be approximately equal to the threshold amount. Thus, when the amount of analyte in the sample is even slightly below the threshold concentration, an extreme signal condition (either maximum or no signal) will be produced in a subsequent detection phase of the assay. Conversely, when the amount of analyte in the sample is at or above the threshold amount, there will be a predictable minimum residual amount of analyte, and the detection phase of the assay will be designed to provide the opposite extreme signal condition.

The method and kit of the present invention are thus useful for performing tests where it is desired to know whether or not the threshold concentration of analyte is present or exceeded in the sample being tested. The method and kit are further useful for performing semi-quantitative assays where two or more threshold concentrations are detected simultaneously, from a single sample. In both cases, the tests may be conveniently performed by untrained and semi-trained individuals. Sample preparation is usually minimal, and the assay method steps may be easily performed by an individual reading a set of instructions accompanying the assay kit. In some cases, the test protocols can provide for single-step assays where the sample need only be applied to a test article and visual result read or the article after some reaction time. The assays of the present invention can provide for enhanced sensitivity and readability, and in particular the very large change in signal occurs in a positive assay is particularly helpful in assuring that the test results are easily read and understood even by untrained persons.

The present invention is useful in assaying for a wide variety of analytes in virtually any type of sample which is liquid, which can be liquified, or which can be suspended in a liquid. The method and kit will find their greatest use with biological specimens, such as blood, serum, plasma, urine, cerebral fluid, spinal fluid, ocular lens liquid (tears), saliva, sputum, semen, cervical mucus, scrapings, swab samples, and the like. Use will also be found with industrial, environmental and food samples, such as water, process streams, milk, meat, poultry, fish, conditioned media, and the like. Under certain circumstances, it may be desirable to pretreat the sample, such as by liquification, separation, dilution, concentration, filtration, chemical treatment, or a combination thereof, in order to improve the compatibility of the sample, with the remaining steps of the assay. The selection and pretreatment of biological, industrial, and environmental samples prior to immunological testing is well known in the art and need not be described further.

The analyte to be detected may be virtually any compound, composition, aggregation, or other substance which may be immunologically detected. That is, the analyte, or portion thereof, will be antigenic or haptenic having at least one determinant site, or will be a member of a naturally-occurring binding pair, e.g., carbohydrate and lectin, hormone and receptor, complementary nucleic acids, and the like. Analytes of particular interest include antigens, antibodies, proteins, carbohydrates, haptens, drugs, hormones, hormone metabolites, macromolecules, toxins, bacteria, viruses, enzymes, tumor markers, nucleic acids, and the like, although other types of substances may also be detected. A non-exhaustive list of exemplary analytes is set forth in U.S. Pat. No. 4,366,241, at column 19, line 7 through column 26, line 42, the disclosure of which is incorporated herein by reference.

The present invention is useful for the detection of both large and small molecules, particularly with small molecules having a molecular weight below about 5,000 daltons which will usually be sequestered by a single binding site on the anti-analyte. Larger analytes may bind more than one anti-analyte molecule and, more problematically, may bind a variable number of anti-analyte molecules, rendering the assay unrepeatable. Exemplary small molecules include hormone metabolites, such as pregnanediol-3-glucuronide (PDG), estrone-3-glucuronide, and the like, as well as therapeutic drugs, such as digoxan, phenobarbitol, phenytoin; and drugs of abuse, their metabolites, and the like. Such small molecules will generally be completely sequestered when bound to the anti-analyte. In the case of bivalent antibodies, such as IgG, each antibody molecule will typically sequester two small molecule analytes rendering them unavailable for subsequent detection.

The present invention may also be useful in the detection of larger analytes, i.e., having molecular weights of 5,000 daltons and above, particularly when the analyte is monovalent for the anti-analyte(s) being used. For example, human chorionic gonadotropin (hCG) could be measured using a monoclonal antibody directed to the C-terminal peptide of hCG as the anti-analyte. A predetermined quantity of hCG could be removed using a defined quantity of this antibody. The sample with residual unbound hCG would then be applied to a membrane which had the same antibody to the C-terminal peptide of hCG attached to its surface. Only the residual hCG without anti-hCG antibody would bind to the membrane. The residual hCG would then be detected with a second labeled anti-hCG antibody which was not specific to the C-terminal peptide, e.g., antibody to the α subunit of hCG.

The anti-analyte will be a specific binding substance capable of binding directly or indirectly to the analyte with a high affinity, typically being at least about $10^8$ M$^{-1}$, usually being at least about $10^9$ M$^{-1}$, and sometimes being $10^{10}$ M$^{-1}$ or greater. The anti-analyte should be free from cross-reactivity with other substances that may be present in the sample or the assay reagents. Most commonly, the anti-analyte will be a monoclonal or polyclonal antibody raised against the analyte, but in some cases it may be possible to employ natural receptors for biological analytes, as described above. In cases where the analyte is itself an antibody, it will of course be possible to employ antigens or haptens recognized by the antibody as the anti-analyte.

While the anti-analyte will most often bind directly to the analyte, the present invention also comprises indirect binding of anti-analyte to analyte, i.e., the use of one or more intermediate binding substances to sequester or effect a linkage to the analyte. For example, when binding to a solid phase, it will be possible to provide a primary binding substance, e.g., avidin or a primary antibody, on the solid phase which is able to bind directly a soluble substance which is specific for the analyte, e.g., a biotinylated antibody or secondary antibody which recognizes the analyte. A wide variety of such indirect binding protocols are available and well described in the scientific and patent literature. The term "anti-analyte" as used in the specification and claims are thus intended to include all substances which are able to bind the analyte, either directly (i.e., without an intermediate binding substance) or indirectly (i.e., with one or more intermediate binding substances forming a linkage).

The first step of the assay of the present invention comprises reacting a sample suspected of containing the analyte with a preselected first amount of the anti-analyte selected to reduce the amount of available free analyte in the reacted sample by a preselected differential amount. The differential amount is selected to leave a residual amount of analyte which, when analyte was initially present in the sample at or above the threshold concentration, will be sufficient to provide an extreme signal condition during the detection phase of the assay. Conversely, when the analyte was initially present in the sample below the threshold concentration, there will be little or no residual analyte and the result will be an opposite extreme signal condition during the detection phase of the assay. An "extreme signal condition" will usually be the presence or absence of a visual signal, such as color production, fluorescence, luminescence, and the like, as described in more detail hereinbelow.

Reaction between the free analyte and the first amount of anti-analyte may be effected in a variety of ways. For example, the first amount of anti-analyte may be free (unbound) and present in a suitable buffer or other liquid carrier and combined with the sample. Alternatively, the first amount of the anti-analyte may be present on a solid phase, such as particles, beads, a dipstick, an agarose gel, or the like, and combined with the liquid sample.

In many cases, however, it may be desirable to employ an immobilized first amount of anti-analyte, where the immobilized anti-analyte may be exposed to the sample during the course of another assay step, e.g., sample transfer, sample application, or the like. In particular, the first amount of anti-analyte may be bound to the interior of a transfer pipette or filter used to apply sample to a solid phase membrane, as described in more detail below. Such transfer pipettes and filters are described in detail in U.S. Pat. No. 4,818,677, the disclosure of which has previously been incorporated herein by reference. Transfer pipettes having internal filter matrices suitable for immobilizing the first amount of anti-analyte are described in copending application Ser. No. 07/604,398, the disclosure of which is incorporated herein by reference. Alternatively, the first amount of anti-analyte may be immobilized in the application zone and/or between the application zone and the reaction zone in a lateral flow membrane assay system, as described in U.S. Pat. No. 4,943,522 and copending application Ser. No. 07/639,967, the disclosures of which are incorporated herein by reference.

In any case, the amount of anti-analyte necessary to remove the desired differential amount of native analyte depends on several factors, including (1) the valency of the anti-analyte, (2) the affinity of the anti-analyte, (3) the valency and/or size of the analyte, and (4) the valency and presence of any intermediate binding substances. In the most common case of high affinity IgG antibodies used to directly bind and sequester small molecule analytes, such as hormone metabolites and drugs, the valency of the anti-analyte is two, while the "valency" of the analyte is one, i.e., it is sufficiently small that it presents only one binding site to the antibodies. The high affinity nature of the anti-analyte assures that substantially all antibody binding sites will be occupied by analyte (so long as there is sufficient analyte in the sample).

Generally, it will be desired to remove a major portion of the native analyte from samples where the analyte is present at the threshold concentration. The amount of analyte removed or potentially removed, however, will be a constant so that in cases where analyte concentrations greatly exceed the threshold concentration, the proportion of native analyte removed will be much lower. Conversely, in cases where the native analyte is significantly below the threshold concentration, substantially all analyte will be sequestered usually with excess anti-analyte remaining. The optimum percentage of native analyte sequestration will vary depending on the particular analyte and the detection system and may be determined empirically to provide the transition between extreme signal conditions at the desired threshold concentration of analyte.

The reaction between the sample and first amount of the anti-analyte will usually be allowed to proceed (optionally but not necessarily reaching equilibrium) prior to any subsequent assay steps, usually proceeding for at least about ten seconds, more usually requiring at least one to two minutes. After the reaction has occurred, the subsequent assay steps will be initiated, usually without separation of the native analyte bound to the first amount of anti-analyte. It would be possible, however, to effect such separation, particularly when the first amount of anti-analyte has been immobilized on a solid phase. In cases where the sample is only briefly exposed to the first amount of anti-analyte, e.g., when the anti-analyte is immobilized in a transfer pipette or in the introduction zone of a lateral flow membrane, it will be necessary to choose high affinity binding substances and design rapid system kinetics to assure sufficient and consistent binding prior to performance of further steps at the assay.

After reaction between the native analyte and the first amount of anti-analyte has been achieved, the reacted sample is contacted with a second amount of anti-analyte immobilized on a solid phase. In this way, residual free analyte remaining in the reacted sample (i.e., analyte which has not been sequestered by the first amount of anti-analyte) will become bound to the solid phase. The solid phase may be particles, beads, a dipstick, an agarose gel, a microtiter well, or any of a wide variety of other insoluble materials or structures which are commonly employed in heterogeneous immunoassays. Preferred is the use of a membrane solid phase as described in detail hereinbelow.

In a first preferred embodiment, the assay is performed on a perpendicular flow membrane, as described generally in U.S. Pat. No. 4,818,677, the disclosure of which has previously been incorporated herein by reference. The second amount of anti-analyte is immobilized within a detection zone on the membrane and is limited so that its capacity to bind residual free analyte is limited. In particular, it is desirable that the second amount of anti-analyte which is immobilized on the membrane be just sufficient to bind the expected residual amount of native analyte present in the reacted sample when the threshold concentration of native analyte was present in the original sample. In this way, samples which contain native analyte at the threshold concentration or above will block substantially all binding capacity of the second amount of anti-analyte on the membrane. Conversely, when the actual analyte concentration in the sample falls marginally below the threshold concentration, there will be no residual free analyte in the reacted sample and there will be no blocking of the binding capacity of the anti-analyte on the solid phase. It is this aspect of the assay which allows an abrupt change between the extreme signal conditions based on relatively small changes in analyte concentration. Samples at the threshold concentration or above result in a membrane which is completely blocked, while samples which are below the threshold concentration by a small (selectable) amount result in a membrane which retains substantially full binding capacity.

The porous membrane is usually a microporous membrane which is part of a reaction cell including an absorbant in liquid receiving relationship with the membrane. The microporous membrane will have the second amount of anti-analyte immobilized thereon is intended to bind and separate the analyte from the sample which is applied to the membrane as part of the assay protocol. The shape and dimensions of the membrane are not critical, but the membrane should have a sufficiently large exposed area to allow subsequent visualization of bound label on a portion thereof, usually having sufficient excess area so that contrast between a visual signal and the remainder of the membrane may be easily observed.

The microporous membrane may be formed from a wide variety of semi-permeable membrane materials, including organic polymers, such as nylon, polyvinyl chloride, polypropylene, and copolymers thereof; sintered glass and ceramic materials; and the like. The average pore diameter of the material is usually not critical, although materials pore diameters in the range from about 0.2 to 10 μm will generally be suitable, usually being in the range from about 1 to 5 μm.

The second amount of anti-analyte will generally be sufficient to bind to the expected amount of residual native analyte which remains after reaction of the sample with the first amount of anti-analyte. Thus, the second amount of anti-analyte needed will depend on this expected residual value which is determined by the specific assay design.

The membrane having the immobilized second amount of anti-analyte will remain in contact with the combined sample for a time sufficient to achieve binding between the residual free analyte (if any) and the immobilized anti-analyte. Typically, contact will be maintained for up to about one minute, and may be maintained for two minutes or longer. After binding has occurred, the amount of bound analyte will be determined.

In the case of large multivalent analytes, i.e., those containing two or more binding sites, a variety of two-site (sandwich) detection techniques exist. Such two-site detection relies on introducing a detectable label to the analyte bound on the membrane surface, typically by using a labelled anti-analyte. Optionally, various signal amplification techniques could be employed. For example, a primary antibody specific for the analyte could first be introduced, with secondary labelled antibodies specific for the primary antibody being subsequently introduced. Alternatively, biotinylated primary antibodies can be introduced followed by the introduction of labelled avidin. The use of such two-site detection techniques are well described in the patent and scientific literature. See, for example, U.S. Pat. Nos. 4,228,237; 4,298,685; and 4,684,609, the disclosures of which are incorporated herein by reference.

In the case of small analytes, i.e., those which do not allow for secondary binding, it will be preferred to specifically bind label to the remaining anti-analyte on the detection zone of the membrane surface. Conveniently, this can be done by contacting the membrane surface with label conjugated to the analyte or an analyte analog. This results in the binding of label to the solid phase which is inversely related to the presence of native analyte in the sample. That is, analyte concentrations in the sample which are equal to or exceed the threshold concentration will result in no label being bound to the solid phase surface (since all binding sites will have been blocked with residual native analyte) while analyte concentrations which fall below the threshold concentration by a marginal amount will result in the binding of label to all anti-analyte on the solid phase (since the first amount of antibody will have sequestered all available native analyte to prevent its binding to the solid phase).

The analyte will be derivatized to facilitate covalent or noncovalent binding to the label. Usually, the label will be covalently bound by well known techniques. See, for example, the description in U.S. Pat. No. 4,299,916, col. 23, line 61 through col. 24, line 51, the disclosure of which is incorporated herein by reference. A specific method for binding an enzyme label to a PDG analog is described in the Experimental section hereinafter. Alternatively, the analyte may be derivatized to include an intermediate binding substance, such as biotin, avidin, or the like, and a label introduced using an associated receptor for such intermediate binding substance. In some cases, the analyte which forms a part of the analyte-labelled conjugate may be further modified to effect its binding affinity to the anti-analyte immobilized on the solid phase surface. For example, it may be desirable to reduce the binding affinity of the analyte-label conjugate to below the binding affinity of the anti-analyte for the native analyte. In this way, any tendency for the labelled analyte to replace the previously bound native analyte will be reduced or eliminated. Such a modified analyte-label conjugate having reduced binding affinity is exemplified in the Experimental section hereinafter.

The label will usually be part of a signal producing system capable of generating a detectable visual signal on the solid phase surface. Such visual labels include colored particles, color-generating systems, fluorescent systems, and luminescent systems. Suitable signal producing systems will include at least one component and may comprise two or more components, including enzymes, substrates, catalysts, enhancers, and the like. Usually at least one component of the signal producing system will be attached as the label to the analyte or analyte analog and will thus be bound to the solid phase in the detection phase of the assay of the present invention. Numerous suitable signal producing systems are described in the patent and scientific literature. See, for example, U.S. Pat. No. 4,366,241, col. 27, line 35 through col. 36, line 63, the disclosure of which is incorporated herein by reference. The use of color-producing systems which result in the deposition of a dye on the solid phase is preferred. In the examples which follow, PDG analyte conjugated to alkaline phosphatase is bound to the solid phase as the label by the method as previously described. Subsequent exposure of the solid phase membrane to an indoxyl phosphate substrate results in the deposition of a dark blue dye on the membrane solid phase when label has been bound to the membrane as a result of low analyte concentrations in the sample tested.

A second preferred embodiment of the present invention employs a lateral flow membrane assay system, such as those described in U.S. Pat. No. 4,943,522, and copending application Serial No. 07/639,967, the disclosures of which have previously been incorporated herein by reference.

Other lateral flow assay systems which can be modified according to the present invention are described in U.S. Pat. No. 4,861,711; published European patent application 306 772; British patent application 2,204,398; and European patent application 276 152, the disclosures of each being fully incorporated herein by reference.

Such lateral flow membrane assay systems will generally utilize an elongate membrane having an application zone spaced laterally apart from an indicator zone. The membrane permits flow of sample from the application zone to the indicator zone, typically by capillary induced flow. The membrane itself may by bibulous, in which case it may also be chromatographic, but will preferably be non-bibulous so that the flow of analyte and other components is unimpeded. Details for the selection of particular membrane materials are described in the patent publications which have previously been incorporated herein by reference.

Anti-analyte or other capture reagents specific for the analyte will be present within the indicator zone so that analyte will be complexed or bound within the zone as the sample flows through. The lateral flow assay systems will further provide for visualizing the captured analyte within the indicator zone, typically employing components which are incorporated in the membrane itself so that a one-step assay can be performed. For example and preferably, membrane may contain colored substances which are carried by the sample flow through the membrane and which bind to the analyte complexed within the indicator zone. In this way, a one-step assay protocol can be performed where the endpoint is color observed in the indicator zone. That is, the user need only apply sample to the applicator zone, wait a predetermined period, and thereafter observe the presence (or absence) of color within the indicator zone to read the assay results. Other detection systems could be utilized including those described generally and above with the perpendicular flow membrane embodiment of the present invention. Other suitable detection systems are described in detail in the patent publications which have been incorporated herein by reference.

The present invention provides for improved lateral flow membrane assay systems, where the sample will be prereacted to remove or sequester a desired differential amount of the analyte, as described in general above. The removal or sequestration of the analyte may be performed by any of the methods described above for the perpendicular flow membrane assay system. Preferably, the prereaction can be effected by immobilization of the first amount of anti-analyte within the application zone of the membrane and/or within the region of the membrane between the application zone and the indicator zone. This way, the reaction between the analyte in the sample and the first amount of anti-analyte will be effected during the sample application step and optionally during the flow of sample through the membrane. The lateral flow assay can thus be performed without the need of adding a separate incubation of sample with the first amount of anti-analyte. This is particularly important for one-step assay protocols since there will be no need for a second assay step.

Methods for immobilizing the anti-analyte within the application zone or elsewhere within the membrane will be identical to those described for immobilization of the anti-analyte in the indicator zone in the various patent publications which have been incorporated herein by reference.

In a preferred aspect of the present invention, a semi-quantitative analyte measurement can be made by subjecting different aliquots of the sample to different concentrations of the first amount of anti-analyte. Thus, the assay can be adapted to simultaneously detect a plurality of threshold analyte concentrations which in turn permits the analyte concentration to be detected within desired ranges. The number and precision of the ranges can be selected by the user by employing appropriate first amounts of anti-analyte. Such semi-quantitative assays may be advantageously run with the lateral flow membrane assay systems, where different first amounts of anti-analyte are bound within different regions of the applicator zone. The different regions of the applicator zone, in turn, are arranged so that the sample will flow down segregated lanes in the membrane, where one lane is associated with each region of the applicator zone. This way, corresponding zones within the indicator zone will each refer to a different threshold concentration.

Semi-quantitative assays may also be run using the perpendicular flow assay systems of the present invention. For example, a plurality of aliquots of the sample may each be reacted with a different first amount of anti-analyte immobilized in a different region within the detection zone, corresponding to a desired threshold detection. By applying each aliquot of reacted sample to a different region of the membrane, the different regions can be simultaneously detected and visualized and the range of concentration present in the initial sample determine. Conveniently, such an assay can be run using a multiple compartment filter applicator, of the type described in U.S. Pat. Nos. 4,818,677 and 5,079,170, the disclosures of which are incorporated herein by reference.

A kit according to the present invention will include at least a solid phase having the second amount of anti-analyte bound to a surface thereof, container(s) holding necessary liquid reagent(s), sample applicator(s), and instructions which set forth the method steps generally as set forth above. Usually, all components of the kit will be contained in a package.

The following examples are offered by way of illustration, not by way of limitation.

EXPERIMENTAL Materials

*Escherichia coli* alkaline phosphatase was obtained from Worthington Co., Freehold, N.J. (Catalog No. BAPF). Pregnanediol glucuronide (PDG) and pregnenolone glucuronide (PNG) were obtained from Steriods, Inc., Wilton N.H. (Catalog Nos. P6040 and 5520). Reagents required for preparation of conjugates were sulpho-N-hydroxysuccinimide (Aldrich, Milwaukee, Wis., Catalog No. 13067-2); 1-ethyl 1-3-(3-dimethylaminopropyl)-carbodiimide hydrochloride (Sigma Co., St. Louis, Mo., Catalog No. E7750), and dimethlformamide (DMF), (Alrich Co., Catalog No. 15481-4).

Methods

Alkaline Phosphatase Pregnenolone Glucuronide Conjugate

A conjugate of alkaline phosphatase and pregnenolone glucuronide (PNG) was made as follows. 5.2 mg of pregnenolone glucuronide, 3.8 mg of sulpho-N-hydroxy succinamide ester, and 4.4 mg of 1-ethyl-3-(3-dimethylaminopropyl)-carbodiimide in 2 ml of dry DMF were mixed overnight in an air-tight container to produce an active ester of PNG. Alkaline phosphatase was dialysed against 0.1M sodium bicarbonate buffer, pH 8.5. The dialysed alkaline phosphatase (60 mg) was mixed with PNG ester by slow addition of the ester. The conjugate was purified on G-25 column to remove the excess reactants. The purified PNG-alkaline phosphatase conjugate was stored in buffer containing proteins for long term stability.

Reaction Cells

Reaction cells were assembled and spotted with antibody as described in U.S. Pat. No. 4,818,677. Briefly, activated nylon membranes (Biodyne-C) were layered on top of an absorbent. The membrane and absorbent were separated by an inert porous spacer layer. The whole assembly of membranes was sandwiched between two plastic strips which were welded together. The top plastic layer included a large orifice to permit application of antibodies and solutions. One μl of anti-PDG antibody (4 mg/ml) was applied to the membrane. The remaining binding sites on the membrane were blocked using casein solution. The reaction cell strips were dried in a vacuum chamber and cut into individual reaction cells.

Assay Protocol

PDG standards were prepared in phosphate buffered gelatin for testing. These standards (200 μl) were incubated with 0, 50 or 100 μg of lyophilized anti-PDG antibody for 2 minutes. At the end of 2 minutes all the reaction mixture was added to the reaction cell which has the immobilized anti-analyte on a membrane. Analyte not bound to free anti-analyte from the first step bound the immobilized antibody on the solid phase. This step was 1 minute. 150 μl of conjugate (PNG-alkaline phosphate) was added to the reaction cell and incubated for 1 minute. The substrate was added with another 1 minute incubation. The reaction was terminated by the addition of 300 μl of water. The color intensity of the test spot was recorded using a Macbeth transmittance monitor.

Results

The assays were performed as described above. The optical density (O.D.) of the test spots were read after the membranes were dried at 45° C. The O.D.'s obtained at different concentrations of PDG is shown in Table 1 and FIG. 1.

TABLE 1

| PDG | Δ Test O.D. | | |
|---|---|---|---|
| μg/ml | 0 μg | 50 μg | 100 μg |
| 0 | 1.09 | 1.04 | 1.12 |
| 1.0 | 0.58 | 0.96 | 1.13 |
| 2.0 | 0.37 | 0.72 | 1.01 |
| 3.0 | 0.25 | 0.47 | 0.91 |
| 4.0 | 0.20 | 0.30 | 0.61 |
| 5.0 | 0.16 | 0.18 | 0.34 |
| 6.0 | 0.14 | 0.15 | 0.20 |

As can be seen, the addition of different amounts of free antibody effectively shifts the concentration range over which the assay changes from positive to negative, with the amount of shift being generally proportional to the amount of free antibody added to the test.

Although the foregoing invention has been described in detail for purposes of clarity of understanding, it will be obvious that certain modifications may be practiced within the scope of the appended claims.

What is claimed is:

1. An assay for determining the presence of a threshold amount of an analyte in a sample, said assay comprising:

reacting the sample with a first amount of unlabeled anti-analyte selected to produce a reaction medium free from label and to reduce the amount of free analyte in the reaction medium by a preselected differential amount;

contacting the reaction medium with a second amount of anti-analyte immobilized on a solid phase, whereby residual free analyte remaining in the reacted sample is bound to the solid phase; and detecting analyte bound to the solid by observation of a separately introduced label phase.

2. An assay as in claim 1, wherein the sample is reacted with the first amount of anti-analyte by combining the sample with anti-analyte in a liquid phase prior to contact with the immobilized second amount of anti-analyte.

3. An assay as in claim 1 wherein the sample is reacted with the first amount of anti-analyte bound to a solid phase.

4. An assay as in claim 1, wherein bound analyte is detected by producing an observable signal related to the amount of analyte bound to the solid phase.

5. An assay as in claim 4, wherein an extreme signal condition is produced when the amount of analyte present in the sample is less than the preselected differential amount.

6. An assay as in claim 5, wherein an opposite extreme signal condition is produced when the amount of analyte present in the sample exceeds the differential amount.

7. An assay as in claim 1, wherein the differential amount is selected to permit detection of bound analyte only when the amount of analyte in the sample exceeds the threshold amount.

8. An assay as in claim 7, wherein the second amount of anti-analyte is selected to bind an amount of analyte equal to the difference between the threshold amount and the differential amount.

9. An assay as in claim 1, wherein the analyte is a small molecule selected from the group consisting of hormones, hormone metabolites, and drugs.

10. An assay as in claim 9, wherein the anti-analyte is an antibody having a binding affinity to the small molecule of at least about $10^8$ $M^{-1}$.

11. An assay for determining the presence of a threshold amount of analyte in a sample, said assay comprising:

applying a quantity of the sample directly to a test region on a porous membrane and permitting the sample to be drawn substantially perpendicularly through said membrane, wherein the test region comprises immobilized anti-analyte and the quantity of sample had been reacted with a first amount of anti-analyte prior to being applied to the test region wherein the first amount of anti-analyte is selected to reduce the amount of analyte in the test sample to a quantity which will fully bind to the immobilized anti-analyte without excess when the threshold amount of analyte is present in the sample, and thereafter applying a label bound to analyte or anti-analyte to detect analyte bound to the test region.

12. An assay as in claim 11, wherein the sample is applied to the test region using an applicator having the first amount of anti-analyte immobilized therein.

13. An assay as in claim 11, wherein the sample is applied to the test region through a filter matrix having the first amount of anti-analyte immobilized therein.

14. An assay as in claim 11, wherein the sample is reacted with the first amount of anti-analyte in a liquid phase prior to applying a quantity of the reacted sample to the test region.

15. An assay as in claim 11, wherein the bound analyte is detected by:

contacting the test region with an analyte-label conjugate, whereby label is bound to the test region inversely with respect to the residual amount of free analyte in the reacted sample; and detecting label bound to the test region.

16. An assay as in claim 15, wherein the label is an enzyme and is detected by contacting the test region with a substrate which produces a visual signal in the presence of the enzyme.

17. An assay for determining the presence of a threshold amount of analyte in a sample, said assay comprising:

applying a quantity of the sample to a liquid application zone on a lateral flow membrane, wherein the quantity is sufficient to cause the sample to flow laterally to an indicator zone on the membrane to permit binding of the analyte to immobilized anti-analyte within the indicator zone, wherein the quantity of sample was reacted with a first amount of anti-analyte prior to being applied to the test region wherein the first amount of anti-analyte is selected to reduce the amount of analyte in the test sample to a quantity which Will fully bind to the immobilized anti-analyte without excess when the threshold amount of analyte is present in the sample, and detecting binding of analyte to anti-analyte within the indicator zone.

18. An assay as in claim 17, wherein the first amount of anti-analyte is immobilized within the application zone, whereby reaction of analyte in the sample with the anti-analyte occurs prior to sample reaching the indicator zone.

19. An assay as in claim 18, wherein the application zone comprises a plurality regions having different amounts of anti-analyte immobilized therein, whereby a plurality of threshold concentrations may be detected in the indicator zone.

20. An assay as in claim 17, wherein the bound analyte in the indicator zone is detected by entrapping detectable particles in a complex formed by the binding of the analyte with the anti-analyte immobilized in the indicator zone.

21. An assay as in claim 20, wherein the detectable particles are selected from the group consisting of colored particles and erythrocytes.

22. An improved specific binding assay of the type wherein an analyte in a sample is combined with immobilized anti-analyte and the amount of analyte determined based on binding between the analyte and the immobilized anti-analyte, wherein the improvement comprises reacting a first amount of unlabeled anti-analyte with sample in the absence of label prior to combination with immobilized anti-analyte whereby only residual analyte which has not been bound by the first amount of anti-analyte is available to bind to the immobilized anti-analyte.

23. An assay as in claim 22, wherein a sufficient amount of free anti-analyte is introduced to permit detection of bound analyte only when the amount of analyte in the sample exceeds the threshold amount.

24. An assay as in claim 22, wherein the analyte is a small molecule selected from the group consisting of hormone metabolites and drugs.

25. An assay as in claim 24, wherein the anti-analyte is an antibody having a binding affinity to the small molecule of at least about $10^8 M^{-1}$.

26. An assay as in claim 22, wherein the analyte and first amount of anti-analyte react directly without the presence of an intermediate binding substance.

27. An assay as in claim 26, wherein the analyte and the immobilized anti-analyte bind directly without the presence of an intermediate binding substance.

28. An assay as in claim 26, wherein the analyte and the immobilized anti-analyte bind indirectly in the presence of at least one intermediate binding substance.

* * * * *